United States Patent [19]

Scherrer et al.

[11] 4,061,587

[45] Dec. 6, 1977

[54] LIQUID CRYSTALLINE CINNAMIC ACID ESTERS

[75] Inventors: Hanspeter Scherrer, Therwil; Arthur Boller, Binningen, both of Switzerland

[73] Assignee: Hoffmann-La Roche Inc., Nutley, N.J.

[21] Appl. No.: 703,489

[22] Filed: July 8, 1976

Related U.S. Application Data

[60] Continuation of Ser. No. 604,573, Aug. 14, 1975, abandoned, which is a division of Ser. No. 529,436, Dec. 4, 1974, Pat. No. 3,927,066.

[30] Foreign Application Priority Data

Dec. 17, 1973 Switzerland .................... 17626/73

[51] Int. Cl.² ............................ C09K 3/34; G02F 1/13
[52] U.S. Cl. ................................ 252/299; 252/408; 350/160 LC
[58] Field of Search ........................ 252/299, 408; 350/160 LC

[56] References Cited

U.S. PATENT DOCUMENTS

| | | | |
|---|---|---|---|
| 3,795,436 | 3/1974 | Boller et al. | 252/299 |
| 3,796,479 | 3/1974 | Helfrich et al. | 252/299 |
| 3,923,857 | 12/1975 | Boller et al. | 252/299 |
| 3,926,834 | 12/1975 | Jones, Jr. et al. | 252/299 |
| 3,927,064 | 12/1975 | Boller et al. | 252/299 |
| 3,927,066 | 12/1975 | Scherrer et al. | 252/299 |
| 3,947,375 | 3/1976 | Gray et al. | 252/299 |
| 3,952,046 | 4/1976 | Scherrer et al. | 252/299 |

FOREIGN PATENT DOCUMENTS

| | | | |
|---|---|---|---|
| 2,321,632 | 11/1974 | Germany | 252/299 |
| 2,234,522 | 1/1973 | Germany | 252/299 |

OTHER PUBLICATIONS

Gray, G. W., et al., Liquid Crystals & Plastic Crystals, vol. 1, John Wiley & Sons, Inc., N. Y., pp. 103-125 (1/74).

Primary Examiner—Benjamin R. Padgett
Assistant Examiner—T. S. Gron
Attorney, Agent, or Firm—Samuel L. Welt; George M. Gould; William G. Isgro

[57] ABSTRACT

Liquid crystalline alkylcinnamic acid p'-cyanophenyl esters, useful, for example, for electro-optical purposes, are described.

21 Claims, No Drawings

LIQUID CRYSTALLINE CINNAMIC ACID ESTERS

This is a continuation of application Ser. No. 604,573, filed Aug. 14, 1975, which is a division of U.S. Pat. application Ser. No. 529,436, filed Dec. 4, 1974, now U.S. Pat. No. 3,927,066, issued Dec. 16, 1975.

BRIEF SUMMARY OF THE INVENTION

The invention relates to liquid crystalline cinnamic acid esters of the formula

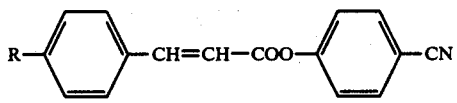

wherein R is straight-chain alkyl of 1 to 8 carbon atoms. The compounds of formula I are useful for electro-optical purposes.

DETAILED DESCRIPTION OF THE INVENTION

The present invention relates to liquid crystalline cinnamic acid esters. More particularly, the invention relates to cinnamic acid esters, nematic mixtures for electro-optical purposes containing same, as well as dielectrics for electro-optical purposes.

The cinnamic acid esters of the invention have the formula

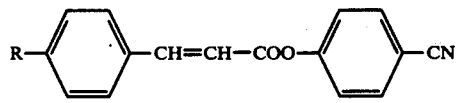

wherein R is straight-chain alkyl of 1 to 8 carbon atoms.

The cinnamic acid esters of formula I can exist not only in trans-form but also in cis-form or as mixtures of the two geometric isomers.

In the trans-form, the cinnamic acid esters of formula I possess nematic properties and, in the liquid crystalline state, a positive anisotropy of the dielectric constants, that is, $\epsilon\|\ > \epsilon\perp$, wherein $\epsilon\|$ is the dielectric constant along the longitudinal axis of the molecule and $\epsilon\perp$ is the dielectric constant perpendicular thereto.

In an electric field, the nematic liquid crystals of formula I of the invention orientate themselves (because $\epsilon\|\ > \epsilon\perp$) with the direction of their largest dielectric constant, that is, with their longitudinal axis, parallel to the field direction. This effect is used, inter alia, in the interaction between embedded molecules and liquid crystalline molecules (guest-host interaction) described by J. H. Heilmeier and L. A. Zanoni [Applied Physics Letters 13, 91 (1968)]. Another interesting application of the dielectric field orientation exists in the rotation cell discovered by M. Schadt and W. Helfrich [Applied Physics Letters 18, 127 (1971)], as well as in the Kerr cell described in Molecular Crystals and Liquid Crystals 17, 355 (1972).

The electro-optical rotation cell is essentially a condenser having transparent electrodes whose dielectric is formed from a nematic substance with $\epsilon\|\ > \epsilon\perp$. The longitudinal axes of the molecules of the liquid crystals are arranged in twisted form between the condenser plates in the fieldless state, the twisted structure being defined by the given wall orientation of the molecules. After the application of an electrical potential to the condenser plates, the molecules adjust themselves with their longitudinal axes in the field direction, i.e., perpendicular to the surface of the plates, by which means linear polarized light is no longer rotated in the dielectric (the liquid crystal is uniaxially perpendicular to the surface of the plates). This effect is reversible and can be used to control electrically the optical transmissivity of the condenser.

In such a "light rotation cell" it is desirable to use compounds which possess a wide nematic range, high stability and slight viscosity and which have no self-coloration. The compounds or mixtures with liquid crystalline properties hitherto utilized always have the disadvantage that at least one of these requirements is not sufficiently satisfied. Surprisingly, it has now been found that the cinnamic acid esters of formula I in trans-form possess liquid crystalline properties which meet all of the foregoing requirements. Said cinnamic acid esters not only have the necessary large or strong positive anisotropy of the dielectric constants, but, especially in the form of their mixtures with one another or with other nematic or non-nematic substances, they have a slight viscosity, a wide nematic range and a high stability. The operation of electro-optical devices is therefore possible using a lower voltage; and the response time is shorter. Moreover, because of their high stability, they can be handled more readily. Still another advantage of the cinnamic acid esters of formula I in trans-form resides in the fact that they form colorless nematic phases.

The cinnamic acid esters of formula I in the cis-form can be used for the preparation of the corresponding trans isomers. In naming of a specific trans cinnamic acid ester of formula I in the following description, the prefix "trans" has been omitted for the sake of simplicity. Accordingly, unless expressly stated to the contrary, only the trans isomer is intended.

Preferred among the cinnamic acid esters of formula I are the trans isomers wherein R is alkyl of 5 to 7 carbon atoms. Especially preferred is the cinnamic acid ester of formula I wherein R is heptyl, namely, p-n-heptylcinnamic acid p'-cyanophenyl ester.

The cinnamic acid esters of formula I prepared by a. reacting a compound of the formula

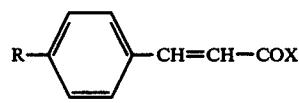

wherein R is as previously described and X is a leaving atom or group
with p-hydroxybenzonitrile or b. dehydrating a compound of the formula

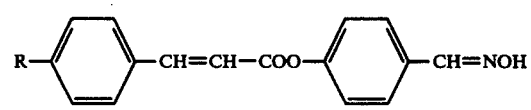

wherein R is as previously described
or c. reacting a compound of the formula

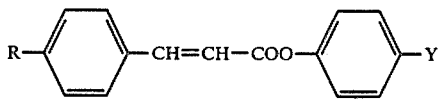

wherein R is as previously described and Y is halogen or arylsulfonyloxy
with copper (I) cyanide or sodium cyanide or d. diazotizing a compound of the formula

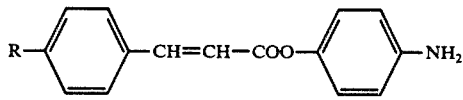

wherein R is as previously described
and reacting the product with copper (I) cyanide or e. converting a cis isomer of formula I into the trans isomer.

As used herein, the term "leaving atom or group" denotes a halogen atom; or lower alkoxy, preferably methoxy or ethoxy; lower alkanoyloxy, preferably formyloxy or acetoxy; aryl-(lower alkoxy), preferably benzyloxy; aryl-(lower alkanoyloxy), preferably benzoyloxy; lower alkylsulfonyloxy, preferably mesyloxy; or arylsulfonyloxy, preferably tosyloxy.

In process embodiment (a) of the invention, a compound of formula II is reacted with p-hydroxybenzonitrile. This reaction is conveniently carried out in an inert organic solvent, for example, an ether such as diethyl ether or tetrahydrofuran; dimethylformamide; benzene; toluene; cyclohexane; carbon tetrachloride; or the like.

In the compound of formula II, X preferably is a halogen atom, particularly chlorine. In order to bind the hydrogen halide liberated in the reaction, an acid binding agent is conveniently utilized. Suitable acid binding agents are tertiary amines, pyridines or the like. The acid binding agent is preferably utilized in a large excess in order that it can simultaneously serve as the acid binding agent as well as a solvent. The temperature and pressure are not critical aspects of the reaction which, in general, is carried out at atmospheric pressure and at a temperature in the range of from room temperature to the boiling temperature of the reaction mixture.

The compounds of formula II wherein X is chlorine can be prepared by reacting an appropriate benzoic acid with thionyl chloride. It is not necessary to isolate these compounds from the mixture in which they are prepared prior to the reaction with p-hydroxybenzonitrile.

In process embodiment (b) of the invention, a compound of formula III is dehydrated. The dehydration is conveniently carried out utilizing acetic anhydride or anhydrous sodium acetate in glacial acetic acid. Advantageously, the dehydration is carried out at the reflux temperature of the mixture. The pressure is not critical although it is desirable to carry out the dehydration at atmospheric pressure.

The compounds of formula III can be prepared by reacting a compound of formula II with p-hydroxybenzaldehyde and reacting the resulting ester with hydroxylamine. The compounds of formula III need not be isolated from the mixture in which they are prepared prior to the dehydration.

In process embodiment (c) of the invention, a compound of formula IV is reacted with copper (I) cyanide or sodium cyanide. This reaction is conveniently carried out in an inert organic solvent, for example, ethyleneglycol, tetrahydrofuran, dimethylformamide, dimethyl sulfoxide, pyridine, acetonitrile or the like. The temperature and pressure at which the reaction is carried out are not critical. However, the reaction is conveniently carried out at atmospheric pressure and at a temperature in the range of from room temperature to the boiling temperature of the reaction mixture.

In the compounds of formula IV, X preferably is a halogen atom, particularly bromine. These compounds can be prepared, for example, by reacting a compound of formula II with p-bromophenol. It is not necessary to isolate the compounds of formula IV from the reaction mixture in which they are prepared prior to the reaction with copper (I) cyanide or sodium cyanide.

In process embodiment (d) of the invention, a compound of formula V is used as the starting material. Such a compound is conveniently diazotized and subjected to a Sandmeyer reaction. The diazotization is carried out in water at a temperature between 0° C. and 5° C. with the addition of hydrochloric acid and sodium nitrite. The diazonium chloride obtained is then subjected to a Sandmeyer reaction. This reaction is conveniently carried out utilizing a solution of, for example, copper (I) cyanide or a complex salt thereof. Conveniently, the reaction is carried out at a temperature in the range of from 0° to 100° C., preferably at a temperature in the range of from 70° to 80° C. The pressure is not critical and the reaction is advantageously carried out at atmospheric pressure.

The compounds of formula V can be prepared by reacting a compound of formula II with N-benzylidene-p-hydroxyaniline and subsequently cleaving the resulting Schiff's base with an aqueous mineral acid.

In process embodiments (a) to (d) there is usually obtained a mixture of trans and cis isomers. The ratio of trans isomers to cis isomers depends on the reaction conditions and mainly on the configuration (cis or trans) of the starting materials of formulas II to IV.

The trans and cis isomers can be separated, for example, by recrystallization or chromatography. The cis isomers can be converted into the trans isomers in the usual manner by heating, treatment with iodine or photochemically. It is not necessary to isolate the cis isomers from the mixture before carrying out the conversion.

The physical properties of the nematic substances of formula I (trans isomers) provided by the present invention are given in the following Table:

TABLE

| R | Melting point | Clearing point |
| --- | --- | --- |
| Methyl | 127° C. | 127.5° C. |
| Ethyl | 104° C. | 117.5° C. |
| n-Propyl | 95.5° C. | 124.5° C. |
| n-Butyl | 82.5° C. | 113.5° C. |
| n-Pentyl | 72.5° C. | 118.5° C. |
| n-Hexyl | 71.5° C. | 106.5° C. |
| n-Heptyl | 57.5° C. | 109.5° C. |
| n-Octyl | 63° C. | 109.5° C.* |

*smectic up to 82.5° C.

The trans-cinnamic acid esters of the invention can be used in the form of mixtures with one another, mixtures which correspond to a eutectic being especially preferred.

The trans-cinnamic acid esters of the invention are preferably used in the form of mixtures with other nematic or non-nematic substances such as, for example, with Schiff's bases of the formula

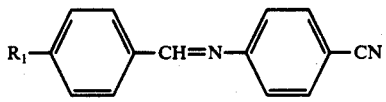

wherein $R_1$ is straight-chain alkyl of 2 to 8 carbon atoms, straight-chain alkoxy of 4 to 7 carbon atoms, straight-chain alkanoyloxy of 2 to 8 carbon atoms or straight-chain alkylcarbonate of 2 to 11 carbon atoms.

Further, the trans cinnamic acid esters of formula I can also be used in the form of mixtures with compounds of the formula

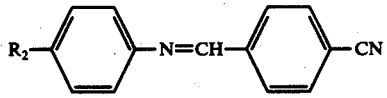

wherein $R_2$ is straight-chain alkyl of 4 to 7 carbon atoms or straight-chain alkylcarbonate of 2 to 11 carbon atoms
or with compounds of the formula

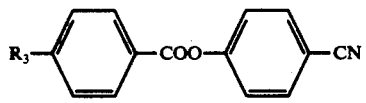

wherein $R_3$ is straight-chain alkyl of 4 to 8 carbon atoms, straight-chain alkoxy of 5 to 8 carbon atoms or straight-chain alkylcarbonate of 3 to 11 carbon atoms
or with compounds of the formula

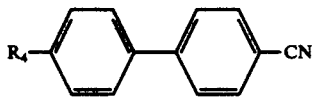

wherein $R_4$ is straight-chain alkyl, for example, n-pentyl, n-hexyl or n-heptyl; straight-chain alkoxy, for example, n-pentyloxy, n-hexyloxy or n-heptyloxy; straight-chain alkanoyloxy of 4 to 9 carbon atoms or straight-chain alkylcarbonate of 4 to 11 carbon atoms.

The compounds of formula VI are known, except, wherein $R_1$ is straight-chain alkylcarbonate are new, and can be obtained by condensing a compound of the formula

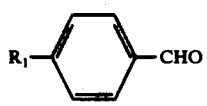

wherein $R_1$ is as previously described
with p-aminobenzonitrile.

The compounds of formula VII are known, except, wherein $R_2$ is straight-chain alkylcarbonate are also new, and can be obtained by condensing a compound of the formula

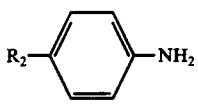

wherein $R_2$ is as previously described
with p-cyanobenzaldehyde.

The compounds of formula VIII are known, except, wherein $R_3$ is straight-chain alkylcarbonate are also new, and can be obtained by reacting a compound of the general formula

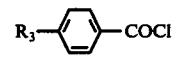

wherein $R_3$ is as previously described
with p-hydroxybenzonitrile.

The compounds of formula IX are known, except, wherein $R_4$ is straight-chain alkanoyloxy or straight-chain alkylcarbonate are also new, and can be obtained by reacting a compound of the formula

$$R'_4COCl \qquad XIII$$

wherein $R'_4$ is alkyl or alkoxy
with 4'-cyano-4-hydroxy-biphenyl.

Especially preferred are the following mixtures: p-n-Heptylcinnamic acid p'-cyanophenyl ester, p-n-hexylbenzoic acid p'-cyanophenyl ester and p-n-octylbenzoic acid p'-cyanophenyl ester in a molar ratio of 1:1:1. Melting point 10° C.; clearing point 71°-71.5° C.

p-n-Heptylcinnamic acid p'-cyanophenyl ester, p-n-pentylbenzoic acid p'-cyanophenyl ester, p-n-heptylbenzoic acid p'-cyanophenyl ester and p-n-octylbenzoic acid p'-cyanophenyl ester in a molar ratio of 1:1:1:1. Melting point 5° C.; clearing point 68–69° C.

p-n-Heptylcinnamic acid p'-cyanophenyl ester, p-n-butylbenzoic acid p'-cyanophenyl ester, p-n-hexylbenzoic acid p'-cyanophenyl ester and p-n-heptylbenzoic acid p'-cyanophenyl ester in a molar ratio of 1:1:1:1. Melting point 0° C.; clearing point 65.5°–66° C.

p-n-Heptylcinnamic acid p'-cyanophenyl ester, p-n-butylbenzoic acid p'-cyanophenyl ester, p-n-hexylbenzoic acid p'-cyanophenyl ester and p-n-octylbenzoic acid p'-cyanophenyl ester in a molar ratio of 1:1:1:1. Melting point 0° C.; clearing point 65° C.

p-n-Heptylcinnamic acid p'-cyanophenyl ester, p-n-hexylbenzoic acid p'-cyanophenyl ester, p-n-octylbenzoic acid p'-cyanophenyl ester and p-[(p-cyano-phenoxy)carbonyl]phenyl n-hexyl carbonate in a molar ratio of 1:1:1:1. Melting point 4° C.; clearing point 71.5°–72° C.

p-n-Heptylcinnamic acid p'-cyanophenyl ester, p-n-heptylbenzoic acid p'-cyanophenyl ester and p-[(p-cyano-phenoxy)carbonyl]phenyl n-hexyl carbonate in a molar ratio of 1:1:1. Melting point 10° C.; clearing point 76°-78° C.

p-n-Heptylcinnamic acid p'-cyanophenyl ester, p-n-heptylbenzoic acid p'-cyanophenyl ester and 4'-n-pentyl-4-cyano-biphenyl in a molar ratio of 1:1:1. Melting point <0° C.; clearing point 69.5°-70° C.

p-n-Heptylcinnamic acid p'-cyanophenyl ester, p-n-heptylbenzoic acid p'-cyanophenyl ester and 4'-n-heptyl-4-cyano-biphenyl in a molar ratio of 1:1:1. Melting point −32° C.; clearing point 70°-70.5° C.

p-n-Heptylcinnamic acid p'-cyanophenyl ester, p-n-hexylbenzoic acid p'-cyanophenyl ester, p-n-octylbenzoic acid p'-cyanophenyl ester and p-[(p-n-heptylbenzyliden)amino]benzonitrile in a molar ratio of 1:1:1:1. Melting point 14° C.; clearing point 70.5°–71° C.

p-n-Heptylcinnamic acid p'-cyanophenyl ester, p-n-heptylbenzoic acid p'-cyanophenyl ester and p-[(p-n-heptylbenzyliden)amino]benzonitrile in a molar ratio of 1:1:1. Melting point 18° C.; clearing point 77° C.

p-n-Heptylcinnamic acid p'-cyanophenyl ester, p-n-hexylbenzoic acid p'-cyanophenyl ester, p-n-octylbenzoic acid p'-cyanophenyl ester and p-methoxy-benzyliden-p'-n-butyl-aniline in a molar ratio of 1:1:1:1. Melting point 3.5° C.; clearing point 64.5° C.

p-n-Heptylcinnamic acid p'-cyanophenyl ester, p-n-heptylbenzoic acid p'-cyanophenyl ester and p-methoxy-benzyliden-p'-n-butyl-aniline in a molar ratio of 1:1:1. Melting point 4° C.; clearing point 71.5° C.

p-n-Hexylcinnamic acid p'-cyanophenyl ester, p-n-butylbenzoic acid p'-cyanophenyl ester, p-n-hexylbenzoic acd p'-cyanophenyl ester and p-n-octylbenzoic acid p'-cyanophenyl ester in a molar ratio of 1:1:1:1. Melting point 5° C.; clearing point 62° C.

p-n-Hexylbezoic acid p'-cyanophenyl ester, p-n-octylbenzoic acid p'-cyanophenyl ester, p-n-hexyloxybenzoic acid p'-cyanophenyl ester and p-n-heptycinnamic acid p'-cyanophenyl ester in a molar ratio of 1:1:1:1. Melting point 4° C.; clearing point 72° C.

p-n-Heptylbenzoic acid p'-cyanophenyl ester, p-n-heptylcinnamic acid p'-cyanophenyl ester and p-[(p-cyanophenoxy)cyanophenyl)carbonyl]phenyl n-hexyl carbonate in a molar ratio of 1:1:1. Melting point 10° C.; clearing point 77° C.

The following examples further illustrate the invention. Examples 11, 12, 13 and 14 illustrate the preparation of compounds of formulas VI, VII, VIII and IX wherein $R_1$, $R_2$, $R_3$ and $R_4$ are straight-chain alkylcarbonate or alkanoyloxy, respectively.

EXAMPLE 1

Preparation of trans p-n-hexylcinnamic acid p'-cyanophenyl ester

The crude p-n-hexylcinnamic acid chloride, obtained by boiling 5.3 g. of p-n-hexylcinnamic acid with thionyl chloride, is dissolved in 35 ml. of absolute benzene and added to 2.9 g. of p-hydroxybenzonitrile in 40 ml. of absolute pyridine. The mixture is heated overnight at 50° C. Then, the mixture is poured on to ice-water and extracted three times with ether. The combined organic phases are washed with dilute hydrochloric acid. Unreacted starting materials are separated using dilute sodium hydroxide solution and the ester solution is washed neutral. The crude product is recrystallized several times from hexane whereby there is obtained pure trans p-n-hexylcinnamic acid p'-cyanophenyl ester having a melting point of 71.5° C. and clearing point of 106.5° C.

The starting material can be prepared as follows:

9.4 G. of p-n-hexylbenzaldehyde in 5 ml. of absolute pyridine are treated with 5.15 g. of malonic acid and 5 drops of piperidine. Then, the mixture is heated at 100° C. for 11 hours, and, subsequently, poured on to cold aqueous hydrochloric acid and extracted with ether. The p-n-hexylcinnamic acid obtained after recrystallization of the crude product from hexane/ether has a melting point of 107°–109° C.

EXAMPLE 2

Preparation of trans p-methylcinnamic acid p'-cyanophenyl ester 1.9 G. of p-methylcinnamic acid chloride in 5 ml. of absolute benzene are added to 1 g. of p-hydroxybenzonitrile in 5 ml. of absolute pyridine. The mixture is stirred for about 60 hours at room temperature, then poured on to ice-water and extracted with ether. The organic phase is washed successively with dilute hydrochloric acid, concentrated sodium carbonate solution and water. 2 G. of crude product are chromatographed on silica gel using benzene. The eluates are recrystallized twice from isopropyl ether. The pure trans p-methylcinnamic acid p'-cyanophenyl ester obtained melts at 127° C. and has a clearing point of 127.5° C.

The starting material can be prepared as follows:

p-Methylcinnamic acid, prepared in a manner analogous to that described in Example 1, is boiled under reflux with thionyl chloride. The residue solidifying after distillation of the excess thionyl chloride is recrystallized from ethyl acetate. The desired acid chloride obtained has a melting point of 71° C.

EXAMPLE 3

Preparation of trans p-ethylcinnamic acid p'-cyanophenyl ester 8.8 G. of crude p-ethylcinnamic acid chloride are dissolved in 55 ml. of absolute benzene and added dropwise to 4.4 g. of p-hydroxybenzonitrile in 55 ml. of absolute pyridine at room temperature over a period of about 25 minutes. The mixture is subsequently heated overnight at 55° C., then cooled, poured on to ice-water and extracted with ether. The ether extracts are washed successively with dilute hydrochloric acid, dilute sodium hydroxide solution and water. Recrystallization of the crude product yields trans p-ethylcinnamic acid p'-cyanophenyl ester having a melting point of 104.5° C. and a clearing point of 117.5° C.

The starting material can be prepared as follows:

7.3 G. of p-ethylcinnamic acid, prepared in a manner analogous to that described in Example 1, are boiled under reflux in 150 ml. of thionyl chloride for 30 minutes. The excess thionyl chloride is then removed by distillation. Repeated uptake of the residue in toluene, concentration and drying yields 8.8 g. of crude p-ethylcinnamic acid chloride.

EXAMPLE 4

Preparation of trans p-n-propylcinnamic acid p'-cyanophenyl ester 8.3 G. of crude p-n-propylcinnamic acid chloride and 4.17 g. of p-hydroxybenzonitrile are stirred overnight at 55° C. in 55 ml. of absolute benzene and 55 ml. of absolute pyridine. The mixture is then poured on to ice-water and worked up in the usual manner. After recrystallization of the crude product for 2 hours, there are obtained 5.5 g. of trans p-n-propylcinnamic acid p'-cyanophenyl ester having a melting point of 95.5° C. and a clearing point of 124.5° C.

The starting material can be prepared as follows:

7.5 G. of p-n-propylcinnamic acid, prepared in a manner analogous to that described in Example 1, are boiled with an excess of thionyl chloride for 30 minutes. Concentration, repeated dissolution of the residue in toluene and reconcentration yields 8.3 g. of crude p-n-propylcinnamic acid chloride.

EXAMPLE 5

Preparation of trans p-n-butylcinnamic acid p'-cyanophenyl ester 1.3 G. of crude p-n-butylcinnamic acid chloride in 10 ml. of absolute benzene are added dropwise to 0.55 g. of p-hydroxybenzonitrile in 10 ml. of absolute pyridine. The mixture is stirred at room temperature overnight, subsequently poured on to ice-water and extracted with ether. The organic phase is washed with dilute hydrochloric acid, dilute ice-cold sodium hydroxide solution and water. The crude product is added to a silica gel column which is eluted with benzene. After two recrystallizations of the pure fractions from isopropyl ether, there is obtained trans p-n-butylcinnamic acid p'-cyanophenyl ester having a melting point of 82.5° C. and a clearing point of 115.5° C.

The starting material can be prepared as follows:

1.0 G. of p-n-butylcinnamic acid, prepared in a manner analogous to that described in Example 1, is boiled at reflux with 25 ml. of thionyl chloride for 30 minutes. Toluene is repeatedly added, the mixture concentrated and dried on a rotary evaporator whereby there are finally obtained 1.3 g. of the desired crude acid chloride.

EXAMPLE 6

Preparation of trans p-n-pentylcinnamic acid p'-cyanophenyl ester p-n-Pentylcinnamic acid chloride, prepared by boiling 1.3 g. of p-n-pentylcinnamic acid (obtained in a manner analogous to that described in Example 1) with thionyl chloride, is dissolved in 10 ml. of absolute benzene and added to 0.7 g. of p-hydroxybenzonitrile in absolute pyridine. The mixture is stirred overnight at 50° C. Thereafter, the mixture is poured on to ice-water and extracted with ether. The ether extract is washed with dilute hydrochloric acid, dilute sodium hydroxide solution and water, and subsequently concentrated. After two recrystallization from hexane, there is obtained trans-p-n-pentylcinnamic acid p'-cyanophenyl ester having a melting point of 72.5° C. and a clearing point of 118.5° C.

EXAMPLE 7

Preparation of trans p-n-heptylcinnamic acid p'-cyanophenyl ester 9.9 G. of crude p-n-heptylcinnamic acid chloride in 45 ml. of absolute benzene and 3.57 g. of p-hydroxybenzonitrile in 45 ml. of absolute pyridine are stirred overnight at 55° C. After cooling, the mixture is shaken with ice-water and ether. The organic phase is washed successively with dilute hydrochloric acid, dilute sodium hydroxide solution and water. 11.5 G. of crude product are introduced on to a silica gel column and eluted with hexane/ether (19:1). Pure fractions are collected, treated with active carbon in ethanol and finally recrystallized from hexane. There are thus obtained 8.6 g. of trans p-n-heptylcinnamic acid p'-cyanophenyl ester having a melting point of 57.5° C. and a clearing point of 109.5° C.

The starting material can be prepared as follows:

8.8 G. of p-n-heptylbenzaldehyde and 8.74 g. of malonic acid are dissolved in 7 ml. of absolute pyridine, treated with 8 drops of piperidine and heated at 90°-100° C. for 68 hours. The mixture is then taken up in ether and washed with dilute hydrochloric acid. After recrystallization from ether/hexane, there are obtained 7.5 g. of p-n-heptylcinnamic acid having a melting point of 121°-122° C. and a clearing point of 150°-153° C. 8.2 G. of this acid are boiled at reflux in 120 ml. of thionyl chloride for 30 minutes. The excess thionyl chloride is removed by distillation, the residue taken up three times in absolute toluene, concentrated and dried. The p-n-heptylcinnamic acid chloride obtained can be used in the process directly.

EXAMPLE 8

Preparation of trans p-n-octylcinnamic acid p'-cyanophenyl ester 2.3 G. of crude p-n-octylcinnamic acid chloride in 10 ml. of absolute benzene are added dropwise at room temperature to 0.810 g. of p-hydroxybenzonitrile in 10 ml. of absolute pyridine. Subsequently, the mixture is stirred and heated to 50° C. overnight. The mixture is then poured on to ice-water and extracted with ether. The crude product obtained after washing with dilute hydrochloric acid, dilute sodium hydroxide solution and water is recrystallized twice from hexane whereby there is obtained trans p-n-octylcinnamic acid p'-cyanophenyl ester; melting point 63° C., smectic up to 82.5° C., clearing point 105.5° C.

The starting material can be prepared as follows:

1.8 G. of p-n-octylcinnamic acid, prepared in a manner analogous to that described in Example 1, are boiled in 25 ml. of thionyl chloride for 30 minutes. The excess thionyl chloride is removed by distillation. The residue is taken up twice in absolute toluene, concentrated on a rotary evaporator and dried. There is thus obtained crude p-n-octylcinnamic acid chloride.

EXAMPLE 9

Preparation of trans p-n-heptylcinnamic acid p'-cyanophenyl ester 2.0 G. of p-n-heptylcinnamic acid p'-bromophenyl ester are boiled at reflux with 0.6 g. of copper (I) cyanide in 2.5 ml. of dimethylformamide. While still warm, the mixture is poured on to 1 ml. of ethylenediamine and 3 ml. of water, shaken vigorously for 5 minutes and then extracted three times with benzene. The combined organic extracts are washed twice with an aqueous ethylenediamine solution and several times with water. After recrystallization of the crude product from hexane, there is obtained trans p-n-heptylcinnamic acid p'-cyanophenyl ester having a melting point of 57.5° C. and a clearing point of 105.5 ° C.

The starting material can be prepared as follows:

5.3 G. of p-n-heptylcinnamic acid, prepared in a manner analogous to that described in Example 7, in 25 ml. of benzene are stirred with 5 ml. of thionyl chloride and 0.5 ml. of dimethylformamide for 2 hours at room temperature and subsequently heated at 50° C. for 30 minutes. Absolute toluene is added twice and each time the mixture is concentrated. After drying, there are obtained 6.2 g. of crude p-n-heptylcinnamic acid chloride. Subsequently, 1.55 g. of p-bromophenol in absolute pyridine are treated with an excess of p-n-heptylcinnamic acid chloride in absolute benzene and the mixture is stirred overnight at about 50° C. After cooling, the mixture is poured on to ice-water, extracted with ether and washed successively with dilute hydrochloric acid, dilute sodium hydroxide solution and water. The resulting crude p-n-heptylcinnamic acid p'-bromophenyl ester is recrystallized from ether/hexane.

EXAMPLE 10

Preparation of trans p-n-heptylcinnamic acid p'-cyanophenyl ester 1.9 G. of p-n-heptylcinnamic acid p'-formylphenyl ester are boiled at reflux for 16 hours with 0.56 g. of hydroxylamine hydrochloride and 0.86 g. of anhydrous sodium acetate in 100 ml. of glacial acetic acid, p-n-heptylcinnamic acid p'-oximinophenyl ester initially forming and being subsequently dehydrated. After removal of the major portion of glacial acetic acid by distillation, the residue is taken up in ether and washed thoroughly with water and sodium bicarbonate solution. The crude product is introduced on to a silica gel column. Elution with benzene yields trans p-n-heptylcinnamic acid p'-cyanophenyl ester which, after recrystallization from hexane, has a melting point of 57.5° C., and a clearing point of 110° C.

The starting material can be prepared as follows:

The acid chloride, prepared from 2.45 g. of p-n-heptylcinnamic acid (prepared in a manner analogous to that described in Example 7) by boiling with thionyl chloride, is dissolved in 15 ml. of absolute benzene and added to 1.1 g. of p-hydroxybenzaldehyde in 15 ml. of absolute pyridine. The mixture is heated overnight at about 50° C., treated with ether and washed with dilute hydrochloric acid, dilute sodium hydroxide solution and water. After recrystallization from ether/hexane, there is obtained crude p-n-heptylcinnamic acid p'-formylphenyl ester.

EXAMPLE 11

Preparation of trans p-[N-(p-cyanophenyl)formimidoyl]-phenyl methyl carbonate

A mixture of 6.1 g. of p-formylphenylcarbonic acid methyl ester and 4.0 g. of p-aminobenzonitrile in 100 ml. of benzene is gassed with argon and heated under reflux (bath temperature 135° C.) for 1 hour. The water which forms is separated using a water separator. The benzene condensing in the reflux condenser is then led back into the reaction vessel over a period of an additional 1 hour through a layer of 100 g. of aluminum oxide (activity I). After cooling, the mixture is freed from solvent in vacuo at 50° C. (bath temperature) and there are obtained 9.3 g. of almost colorless crystals. The crystals are recrystallized several times from isopropanol up to a constant melting point and clearing point and until by-products disappear in the gas chromatogram. The resulting pure, colorless trans p-[N-(p-cyanophenyl)formimidoyl]-phenyl methyl carbonate has a melting point of 139°-139.2° C. and a clearing point of 156° C. UV (ethanol): $\epsilon_{274}$ = 24100 (shoulders at 315 and 234 nm; minimum at 242 nm).

EXAMPLE 12

Preparation of trans p-[(p-cyanobenzyliden)amino]phenyl methyl carbonate

A mixture of 0.835 g. of p-methoxycarbonyloxyaniline and 0.655 g. of p-cyanobenzaldehyde in 50 ml. of benzene is gassed with argon and heated under reflux (bath temperature 130° C.) for 1 hour. The resulting water is separated by means of a water separator. The benzene condensing in the reflux condenser is then led back into the reaction vessel over a period of an additional 1 hour through a layer of 20 g. of aluminum oxide (activity I). After cooling, the mixture is freed from solvent in vacuo at 50° C. (bath temperature) and there remain 1.395 g. of yellowish crystals. The crystals are recrystallized several times from isopropanol up to constant melting point and clearing point and until by-products disappear in the gas chromatogram. The pure, slightly yellowish trans p-[(p-cyanobenzyliden)amino]phenyl methyl carbonate obtained has a melting point of 145.1°-146.2° C. and a clearing point of 163.4° C. UV (ethanol): $\epsilon_{270}$ = 20250, $\epsilon_{324}$ = 10800 (shoulders at 243 and 221 nm; minima at 312 and 233 nm).

EXAMPLE 13

Preparation of trans p-[(p-cyanophenoxy)carbonyl]phenyl ethyl carbonate 5.66 G. of p-cyanophenol are dissolved in 66 ml. of absolute pyridine and cooled to −10° C. with stirring. 8.6 G. of crude p-carbethoxy-oxybenzoyl chloride are added portionwise over a period of 10 minutes. The temperature rises to 0° C. and pyridine hydrochloride precipitates out. The mixture is subsequently stirred overnight at room temperature and then poured on to a mixture of 200 ml. of ice and 200 ml. of 20% hydrochloric acid. The mixture is extracted three times with ethyl acetate, the extracts are washed with water, dried over sodium sulfate and evaporated in vacuo. 12.4 G. of reddish crystals are obtained as the residue. The crystals are dissolved in benzene and chromatographed on 400 g. of silica gel. Elution with benzene/1% acetone (v/v) yields 8.1 g. of yellowish crystals which are recrystallized from acetone/hexane up to constant melting point and clearing point. The pure trans p-[(p-cyanophenoxy)carbonyl]phenyl ethyl carbonate obtained melts at 144.7°-144.8° C. and is liquid crystalline (monotrope) upon cooling at 115.8° C. UV (ethanol): $\epsilon_{241}$ = 29700.

The starting material is prepared as follows:

Chloroformic acid ethyl ester is reacted with p-hydroxybenzoic acid in the presence of N-sodium hydroxide according to the method E. Fischer, Ber. 41, 2877 (1908). Thereafter, there is obtained crystalline p-carbethoxy-oxybenzoic acid which is treated with thionyl chloride according to the procedure of H. Schonenberger et al., Arzneimittelforschung 14, 324 (1964). After removal of the excess thionyl chloride in vacuo, there is obtained crude p-carbethoxy-oxybenzoyl chloride which is used directly as described earlier in this Example.

EXAMPLE 14

Preparation of trans 4'-cyano-4-biphenylyl butyrate 0.390 G. of 4'-cyano-4-hydroxy-biphenyl are dissolved in 4.0 ml. of absolute pyridine and cooled to −10° C. with stirring. 0.255 G. of butyric acid chloride are added dropwise over a period of 2 minutes. The temperature rises to 0° C. and pyridine hydrochloride precipitates out. The suspension is subsequently stirred overnight at room temperature and then poured on to a mixture of 12 g. of ice and 12 ml. of 20% hydrochloric acid. The resulting mixture is extracted three times with ethyl acetate, the extracts are washed with water, dried over sodium sulfate and evaporated in vacuo. The residue consists of 0.552 g. of yellowish crystals which are dissolved in benzene and chromatographed on 40 g. of silica gel. Elution with benzene yields 0.521 g. of yellowish crystals which are recrystallized from acetone/hexane up to constant melting point and clearing point.

The pure trans 4′-cyano-4-biphenylyl butyrate obtained melts at 77.9°–78.2° C. and is liquid crystalline (monotrope) upon cooling at 74.7° C. UV (ethanol): ε₂₇₂ = 26100.

We claim:

1. An electro-optical cell containing a nematic composition which comprises a nematic compound of the formula

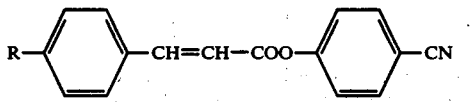

wherein R is straight-chain alkyl of 1 to 8 carbon atoms, or mixtures thereof.

2. A nematic composition for electro-optical purposes, which comprises a compound of the formula

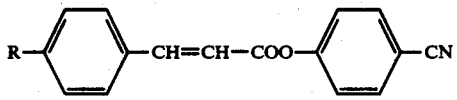

wherein R is straight-chain alkyl of 1 to 8 carbon atoms, or mixtures thereof, and one or more other positive anisotropic nematic compounds.

3. A nematic composition in accordance with claim 2, which comprises a cinnamic acid ester of the formula

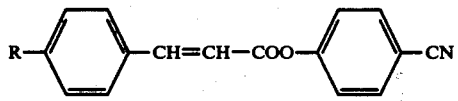

wherein R is straight-chain alkyl of 1 to 8 carbon atoms, or mixtures thereof, and one or more compounds of the formula

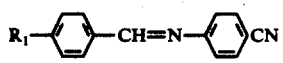

wherein R₁ is straight-chain alkyl of 2 to 8 carbon atoms, straight-chain alkoxy of 4 to 7 carbon atoms, straight-chain alkanoyloxy of 2 to 8 carbon atoms or straight-chain alkylcarbonate of 2 to 11 carbon atoms.

4. A nematic composition in accordance with claim 2, which comprises a cinnamic acid ester of the formula

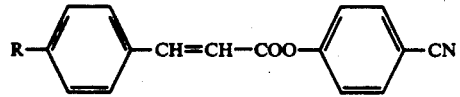

wherein R is straight-chain alkyl of 1 to 8 carbon atoms, or mixtures thereof, and one or more compounds of the formula

wherein R₂ is straight-chain alkyl of 4 to 7 carbon atoms or straight-chain alkylcarbonate of 2 to 12 carbon atoms.

5. A nematic composition in accordance with claim 2, which comprises a cinnamic acid ester of the formula

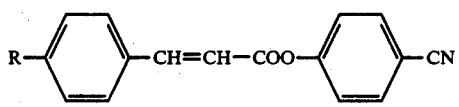

wherein R is straight-chain alkyl of 1 to 8 carbon atoms, or mixtures thereof, and one or more compounds of the formula

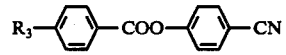

wherein R₃ is straight-chain alkyl of 4 to 8 carbon atoms, straight-chain alkoxy of 5 to 8 carbon atoms or straight-chain alkylcarbonate of 3 to 11 carbon atoms.

6. A nematic composition in accordance with claim 2, which comprises a cinnamic acid ester of the formula

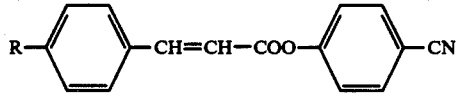

wherein R is straight-chain alkyl of 1 to 8 carbon atoms, or mixtures thereof, and one or more compounds of the formula

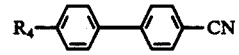

wherein R₄ is straight-chain alkyl, straight-chain alkoxy, straight-chain alkanoyloxy of 4 to 9 carbon atoms or straight-chain alkylcarbonate of 4 to 11 carbon atoms.

7. A nematic composition in accordance with claim 5, which comprises p-n-heptylcinnamic acid p′-cyanophenyl ester, p-n-hexylbenzoic acid p′-cyanophenyl ester and p-n-octylbenzoic acid p′-cyanophenyl ester.

8. A nematic composition in accordance with claim 5, which comprises p-n-heptylcinnamic acid p′-cyanophenyl ester, p-n-pentylbenzoic acid p′-cyanophenyl ester, p-n-heptylbenzoic acid p′-cyanophenyl ester and p-n-octylbenzoic acid p′-cyanophenyl ester.

9. A nematic composition in accordance with claim 5, which comprises p-n-heptylcinnamic acid p′-cyanophenyl ester, p-n-butylbenzoic acid p′-cyanophenyl ester, p-n-hexylbenzoic acid p′-cyanophenyl ester and p-n-heptylbenzoic acid p′-cyanophenyl ester.

10. A nematic composition in accordance with claim 5, which comprises p-n-heptylcinnamic acid p′-cyanophenyl ester, p-n-butylbenzoic acid p′-cyanophenyl ester, p-n-hexylbenzoic acid p′-cyanophenyl ester and p-n-octylbenzoic acid p′-cyanophenyl ester.

11. A nematic composition in accordance with claim 5, which comprises p-n-heptylcinnamic acid p′-cyanophenyl ester, p-n-hexylbenzoic acid p′-cyanophenyl ester, p-n-octylbenzoic acid p′-cyanophenyl ester and p-[(p-cyanophenoxy)carbonyl]phenyl n-hexyl carbonate.

12. A nematic composition in accordance with claim 5 which comprises p-n-heptylcinnamic acid p′-cyanophenyl ester, p-n-heptylbenzoic acid p′-cyanophenyl ester and p-[(p-cyano-phenoxy)carbonyl]phenyl n-hexyl carbonate.

13. A nematic composition in accordance with claim 2 which comprises p-n-heptylcinnamic acid p'-cyanophenyl ester, p-n-heptylbenzoic acid p'-cyanophenyl ester and 4'-n-pentyl-4-cyano-biphenyl.

14. A nematic composition in accordance with claim 2 which comprises p-n-heptylcinnamic acid p'-cyanophenyl ester, p-n-heptylbenzoic acid p'-cyanophenyl ester and 4'-heptyl-4-cyano-biphenyl.

15. A nematic composition in accordance with claim 2 which comprises p-n-heptylcinnamic acid p'-cyanophenyl ester, p-n-hexylbenzoic acid p'-cyanophenyl ester, p-n-octylbenzoic acid p'-cyanophenyl ester and p-[(p-n-heptylbenzyliden)amino]benzonitrile.

16. A nematic composition in accordance with claim 2 which comprises p-n-heptylcinnamic acid p'-cyanophenyl ester, p-n-heptylbenzoic acid p'-cyanophenyl ester and p-[(p-n-heptylbenzyliden)amino]benzonitrile.

17. A nematic composition in accordance with claim 2 which comprises p-n-heptylcinnamic acid p'-cyanophenyl ester, p-n-hexylbenzoic acid p'-cyanophenyl ester, p-n-octylbenzoic acid p'-cyanophenyl ester and p-methoxy-benzyliden-p'-n-butyl-aniline.

18. A nematic composition in accordance with claim 2 which comprises p-n-heptylcinnamic acid p'-cyanophenyl ester, p-n-heptylbenzoic acid p'-cyanophenyl ester and p-methoxy-benzyliden-p'-n-butyl-aniline.

19. A nematic composition in accordance with claim 2 which comprises p-n-hexylcinnamic acid p'-cyanophenyl ester, p-n-butylbenzoic acid p'-cyanophenyl ester, p-n-hexylbenzoic acid p'-cyanophenyl ester and p-n-octylbenzoic acid p'-cyanophenyl ester.

20. A nematic composition in accordance with claim 2 which comprises p-n-hexylbenzoic acid p'-cyanophenyl ester, p-n-octylbenzoic acid p'-cyanophenyl ester, p-n-hexyloxybenzoic acid p'-cyanophenyl ester and p-n-heptylcinnamic acid p'-cyanophenyl ester.

21. A nematic composition in accordance with claim 5 which comprises p-n-heptylbenzoic acid p'-cyanophenyl ester, p-n-heptylcinnamic acid p'-cyanophenyl ester and p-[(p-cyano-phenoxy)carbonyl]phenyl n-hexyl carbonate.

* * * * *